United States Patent
LeLievre et al.

(10) Patent No.: US 9,233,228 B1
(45) Date of Patent: Jan. 12, 2016

(54) MEDICAL APPLIANCE SECURING DEVICE

(75) Inventors: Matthew John LeLievre, Estero, FL (US); Randel B. Holmes, Knoxville, TN (US)

(73) Assignee: M.C. JOHNSON CO., INC., Fort Myers, FL (US)

( * ) Notice: Subject to any disclaimer, the term of this patent is extended or adjusted under 35 U.S.C. 154(b) by 0 days.

(21) Appl. No.: 11/710,770

(22) Filed: Feb. 26, 2007

(51) Int. Cl.
*A61M 25/02* (2006.01)

(52) U.S. Cl.
CPC ......... *A61M 25/02* (2013.01); *A61M 2025/026* (2013.01); *A61M 2025/0253* (2013.01); *A61M 2025/0266* (2013.01)

(58) Field of Classification Search
CPC .......... A61M 25/02; A61M 2025/026; A61M 2025/0266; A61M 2025/0253
USPC .................................. 604/174–180
See application file for complete search history.

(56) References Cited

U.S. PATENT DOCUMENTS

| | | |
|---|---|---|
| 3,430,300 A | 3/1969 | Doan |
| 3,677,250 A | 7/1972 | Thomas |
| 3,826,254 A | 7/1974 | Mellor |
| 4,165,748 A * | 8/1979 | Johnson ........................ 604/180 |
| D252,822 S | 9/1979 | McFarlane |
| 4,333,468 A | 6/1982 | Geist |
| 4,336,806 A | 6/1982 | Eldridge, Jr. |
| 4,563,177 A | 1/1986 | Kamen |
| 4,897,082 A | 1/1990 | Erskine |
| 4,976,700 A | 12/1990 | Tollini |
| 5,147,322 A | 9/1992 | Bowen et al. |
| 5,156,641 A | 10/1992 | White |
| 5,300,037 A | 4/1994 | Delk et al. |
| 5,304,146 A | 4/1994 | Johnson et al. |
| 5,395,344 A | 3/1995 | Beisang, III et al. |
| 5,415,642 A | 5/1995 | Shepherd |
| D364,922 S | 12/1995 | Bierman |
| 5,520,656 A | 5/1996 | Byrd |
| D375,356 S | 11/1996 | Bierman |
| 5,707,703 A * | 1/1998 | Rothrum et al. ............. 428/40.1 |
| D393,903 S | 4/1998 | Bierman |
| 5,810,781 A | 9/1998 | Bierman |
| D401,329 S | 11/1998 | Bierman |

(Continued)

FOREIGN PATENT DOCUMENTS

EP  145142 A1  6/1985

OTHER PUBLICATIONS www.mcjohnson.com/cath-secure.html (information regarding CATH-SECURE medical tube holder, M.C. Johnson Co., Inc., Naples, FL).

*Primary Examiner* — Bhisma Mehta
*Assistant Examiner* — Bradley Osinski
(74) *Attorney, Agent, or Firm* — Kriegsman & Kriegsman

(57) ABSTRACT

A medical appliance securing device. In one embodiment, the device includes a pair of anchoring patches, each of the anchoring patches having an inner edge. A retaining tab extends from and interconnects the inner edges of the anchoring patches. The retaining tab has a first end fixed to the patches and a second end that is free to move relative to patches so that the retaining tab may be wrapped around at least a portion of a medical appliance. Complementary fasteners are adhered to the fixed and free ends of the retaining tab. Both the anchoring patches and the retaining tab are made up of a multi-layer material that includes a breathable non-woven fabric, a pressure-sensitive adhesive adhered to one surface of the fabric, and a moisture-barrier layer adhered to the opposite surface of the fabric.

11 Claims, 5 Drawing Sheets

(56) References Cited

U.S. PATENT DOCUMENTS

| | | | |
|---|---|---|---|
| 5,947,931 A * | 9/1999 | Bierman | 604/180 |
| 5,968,000 A * | 10/1999 | Harrison et al. | 602/41 |
| D424,691 S | 5/2000 | Yavitz | |
| 6,419,660 B1 * | 7/2002 | Russo | 604/180 |
| D492,411 S | 6/2004 | Bierman | |
| 6,827,706 B2 | 12/2004 | Tollini | |
| 6,834,652 B2 | 12/2004 | Altman | |
| D503,977 S | 4/2005 | Bierman | |
| 6,877,167 B2 | 4/2005 | Korkor | |
| 6,929,625 B2 | 8/2005 | Bierman | |
| 6,951,550 B2 | 10/2005 | Bierman | |
| 6,972,003 B2 | 12/2005 | Bierman | |
| 7,090,660 B2 | 8/2006 | Roberts et al. | |
| D528,206 S | 9/2006 | Bierman | |
| D547,862 S | 7/2007 | Dikeman et al. | |
| D567,941 S | 4/2008 | Dikeman et al. | |
| 7,563,251 B2 | 7/2009 | Bierman et al. | |
| 7,591,803 B2 | 9/2009 | Bierman | |
| 7,635,355 B2 | 12/2009 | Bierman | |
| D608,887 S | 1/2010 | Kyvik et al. | |
| 7,648,492 B2 | 1/2010 | Bierman | |
| 8,074,650 B2 | 12/2011 | Steeves et al. | |
| 2006/0041233 A1 | 2/2006 | Bowen | |
| 2006/0217669 A1 | 9/2006 | Botha | |
| 2007/0043326 A1 * | 2/2007 | Navarro et al. | 604/264 |
| 2008/0195050 A1 | 8/2008 | Dickert et al. | |

* cited by examiner

MEDICAL APPLIANCE SECURING DEVICE

BACKGROUND OF THE INVENTION

The present invention relates generally to medical appliance securing devices and more particularly to a novel medical appliance securing device.

Various medical devices, or portions thereof, are shaped as generally tubular members. Examples of such devices include, but are not limited to, catheters, thermometers, intravenous needles, and various types of electrical wires. There is often a need to secure such devices to or near a patient's body so that the devices can appropriately function. For example, catheters, which are generally long, tubular, flexible conduits used to transport various types of fluids to and from the body of a patient, are often laterally and/or longitudinally fixed to the body of a patient to ensure proper placement and functioning of the catheter, as well as to offer some degree of comfort and mobility for the patient. In particular, some medical procedures involving the use of catheters require the application of a tensile force, known as traction, to the catheter, thus making it particularly necessary to firmly secure the catheter in its longitudinal direction.

To secure a catheter or other medical appliance in the manner indicated above, practitioners have often used one or more strips of conventional, medical-grade, adhesive tape to secure a length of the medical appliance directly to the patient's skin. However, this method has its shortcomings as the adhesive tape tends to become loose over time. In addition, each time that one wishes to adjust the placement of the medical appliance or each time that one wishes to remove the medical appliance from the patient, the adhesive tape must be removed from the skin of the patient, thereby frequently causing irritation and discomfort to the patient.

Consequently, various types of medical appliance securing devices have been devised in an effort to provide the desired restraint and to overcome the disadvantages associated with the use of strips of adhesive tape. For example, in U.S. Pat. No. 4,165,748, inventor Johnson, which issued Aug. 28, 1979, and which is incorporated herein by reference, there is disclosed a simple, easily applied, catheter securing device. The catheter securing device includes two main parts having adhesive thereon for temporary attachment to the limb of a patient. In addition, the device includes a narrow bridge connecting the two main parts. The narrow bridge is also provided with adhesive and is foldable on itself to form a double member. Fasteners, such as snap fasteners or VELCRO® hook and loop fasteners, are positioned on the narrow bridge in such a way that the catheter tube may be releasably held by the narrow bridge in a desired orientation to a patient.

Another example of a medical appliance securing device is disclosed in U.S. Pat. No. 4,976,700, inventor Tollini, which issued Dec. 11, 1990, and which is incorporated herein by reference. In this patent, there is disclosed a securing device for securing to a patient's skin or to a support, a medical device such as tubing, a catheter, an intravenous needle, or the like, including an elongated tape having base portions and a central tab formed integrally therewith, pressure-sensitive tape on the base portions and on an exposed window of the tab, and hook and pile fastener portions on opposite sides of the exposed adhesive on the tab and on the base portion facing the exposed adhesive. A method of fabricating a securing device consisting of the steps of providing a strip of pressure-sensitive tape with release paper thereon, cutting out a window in a central portion of the strip of tape, removing release paper from the central portion of the pressure-sensitive tape, folding the central portion on itself to cause the facing exposed pressure-sensitive adhesive parts to adhere to each other and to provide a window of pressure-sensitive tape defined by the window which was cut out with the remainder of the strip forming a base, and securing hook and pile fastener material on opposite sides of the window of pressure-sensitive tape on the tab and on the portion of the securing device adjacent thereto which constitutes a base.

Still another example of a medical appliance securing device is disclosed in U.S. Pat. No. 5,147,322, inventors Bowen et al., which issued Sep. 15, 1992, and which is incorporated herein by reference. In this patent, there is disclosed a securing device for laterally and longitudinally securing generally tubular members having various diameters to any desired location on the surface of a patient's skin or other support. The device comprises an anchoring patch having one surface coated with adhesive for bonding the device to a patient's skin or some other support. A retaining tab is connected to the anchoring patch and contains an aperture such that the retaining tab may be wrapped around the circumference of the tubular member, inserted through the aperture, and firmly secured to the anchoring patch through the use of fastening means.

Still yet another example of a medical appliance securing device is disclosed in U.S. Pat. No. 5,304,146, inventors Johnson et al., which issued Apr. 19, 1994, and which is incorporated herein by reference. In this patent, there is disclosed a device for securing a generally tubular member of a medical appliance to a support surface. In one embodiment, the device comprises an anchoring patch, the anchoring patch including a first segment and a second segment and having a top surface and a bottom surface. The bottom surface is coated with an adhesive for attaching the anchoring patch to the support surface. A pair of flexible retaining tabs extend from and interconnect the inner edges of the first and second segment, the flexible retaining tabs being of sufficient length to helically wrap around the circumference of the generally tubular member and contact the top surface of the anchoring patch. First fasteners are secured to the free ends of the flexible retaining tabs and a pair of complementary fasteners are spaced outwardly relative to the tabs and are secured to the top surface of said anchoring patch. A generally tubular member may be retained in the device either by helically wrapping the flexible retaining tabs around the circumference of the generally tubular member and then coupling together the fasteners or by positioning the generally tubular member between the flexible tabs and the complementary fasteners and looping the retaining tabs over the generally tubular member and then coupling together the fasteners.

Still yet another example of a medical appliance securing device is disclosed in U.S. Pat. No. 6,419,660, inventor Russo, which issued Jul. 16, 2002, and which is incorporated herein by reference. In this patent, there is disclosed a tube holder and a method for manufacturing the tube holder. The tube holder includes a base for attachment to a surface, for example, a patient's skin, and a tab for securing the tube to the base. According to one embodiment, the tube holder includes a first layer having first and second sides and first and second sections, and a second layer having first and second sides and first and second sections. The first sides of the first and second layers are attached to one another in the first sections of the first and second layers, the second sections of the first sides of the first and second layers are unattached to one another, and the first sections of the first and second layers form the tab and the second sections form the base. The tube holder also includes a third layer attached to the second side of the first layer for receiving a tube.

Still a further example of a medical appliance securing device is disclosed in U.S. Patent Application Publication No. US 2006/0041233 A1, inventor Bowen, which was published Feb. 23, 2006, and which is incorporated herein by reference. In this patent application, there is disclosed an apparatus for releasably securing an appliance on or adjacent a person. The apparatus includes a base and a flap or tongue attached to the base. The tongue may be wrapped around portions of an appliance and then attached to the base to releasably secure the appliance to the base. The base is formed from a first layer of material. The tongue is formed from a second layer of material disposed on the first layer. One or more of the layers is formed from medical grade adhesive tape or any other type of generally flexible material compatible with placement on a person's skin. Some embodiments may include multiple tongues to releasably secure one appliance or multiple appliances to a single base.

An example of a commercially available medical appliance securing device is the CATH-SECURE™ medical appliance securing device, which is available from the present assignee, M.C. Johnson Company, Inc. (Naples, Fla.). The CATH-SECURE™ medical appliance securing device, which corresponds generally to the device of U.S. Pat. No. 4,165,748, is formed by cutting a sheet of DURAPORE® surgical tape into two anchoring patches interconnected by a narrow bridge. (DURAPORE® surgical tape, which is commercially available from 3M Corporation (St. Paul, Minn.), is a tape consisting of a woven, polyester cloth backing having an acrylate pressure-sensitive adhesive applied to one surface thereof.) The narrow bridge is then folded onto and adhered to itself to form a double member retaining tab. VELCRO® hook and loop fasteners are then adhered to the double member retaining tab at locations such that a medical tube may be releasably held by the retaining tab in a desired orientation to a patient.

Although the aforementioned CATH-SECURE™ medical appliance securing device and other similar commercially available devices function reasonably well under dry conditions, the present inventors have observed that, under very humid or wet conditions, the VELCRO® hook and loop fasteners tend to peel away from the DURAPORE®-constructed retaining tab and/or anchoring patch to which they are adhered. As a result, these types of medical appliance securing devices typically cannot be worn by a patient while bathing unless appropriate steps are taken to prevent the device from coming into contact with water. As can be appreciated, such steps may be very inconvenient to a patient.

SUMMARY OF THE INVENTION

It is an object of the present invention to provide a novel medical appliance securing device.

It is another object of the present invention to provide a medical appliance securing device that overcomes at least some of the shortcomings associated with existing medical appliance securing devices.

It is still another object of the present invention to provide a medical appliance securing device that is easy to manufacture and easy to use.

Therefore, according to one aspect of the invention, there is provided a medical appliance securing device comprising (a) an anchor, said anchor being adapted to be secured to a surface; (b) a retaining tab, said retaining tab having a first end and a second end, said first end being fixed to said anchor, said second end being free to move relative to said anchor and being appropriately spaced from said first end to permit said retaining tab to be wrapped around at least a portion of a medical appliance; and (c) fastening means for securing said second end of said retaining tab to one of said first end of said retaining tab and said anchor; (d) wherein at least one of said anchor and said retaining tab comprises a multi-layer structure comprising a breathable fabric and a moisture-barrier layer adhered to said breathable fabric.

According to another aspect of the invention, there is provided a medical appliance securing device comprising (a) an anchor, said anchor comprising a pair of patches, each of said patches having a top, a bottom and an inner edge; (b) a retaining tab, said retaining tab extending from and interconnecting said inner edges of said first and second patches, said retaining tab having a first end and a second end, said first end being fixed to said anchor, said second end being free to move relative to said anchor and being appropriately spaced from said first end to permit said retaining tab to be wrapped around at least a portion of a medical appliance; and (c) fastening means for securing said second end of said retaining tab to one of said first end of said retaining tab and said anchor; (d) wherein each of said anchor and said retaining tab comprises a multi-layer structure comprising a breathable fabric, a pressure-sensitive adhesive adhered to a first surface of said breathable fabric, and a moisture-barrier layer adhered to a second surface of said breathable fabric, said second surface of said breathable fabric being opposite to said first surface of said breathable fabric, and wherein said multi-layer structure is oriented in said anchor so that said pressure-sensitive adhesive is located at the bottoms of said patches.

For purposes of the present specification and claims, various relational terms like "top," "bottom," "proximal," "distal," "upper," "lower," "front," and "rear" are used to describe the present invention when said invention is positioned in or viewed from a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1:
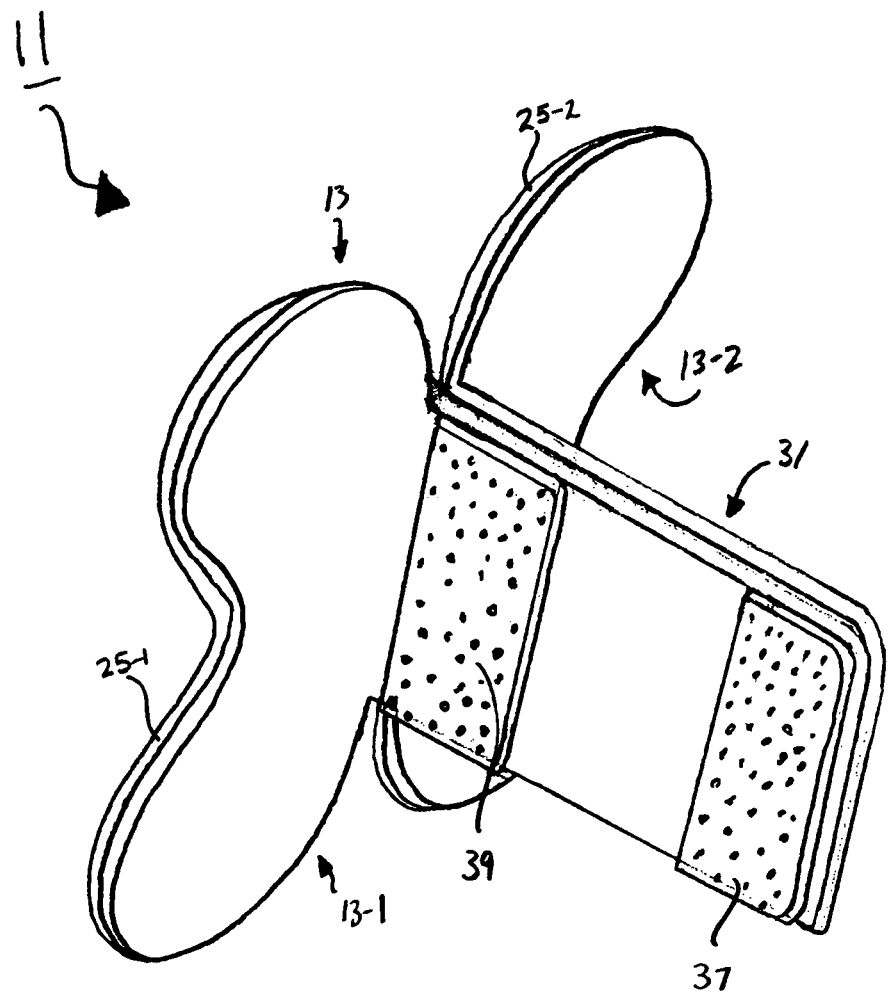
FIG. 1 is a simplified, top, perspective view of a first embodiment of a medical appliance securing device constructed according to the teachings of the present invention.
Figure 2:
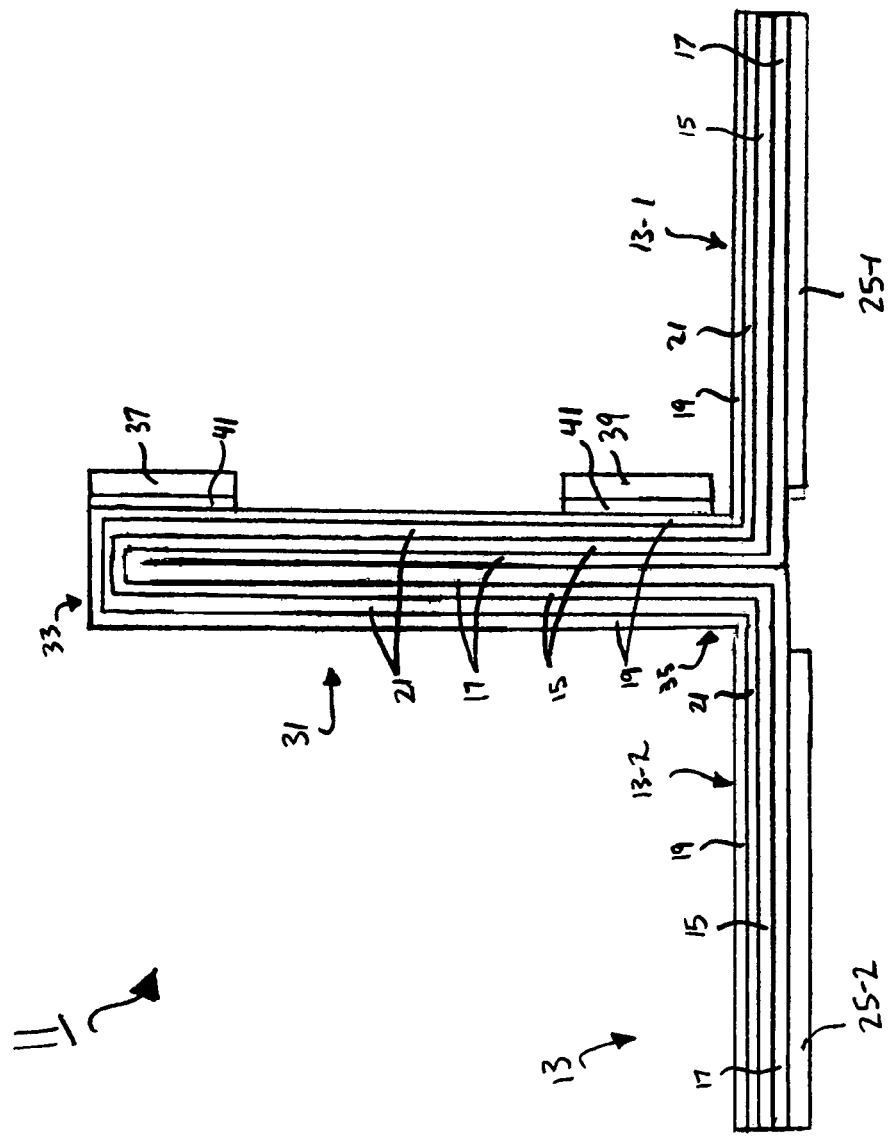
FIG. 2 is a side view of the medical appliance securing device of FIG. 1.
Figure 3:
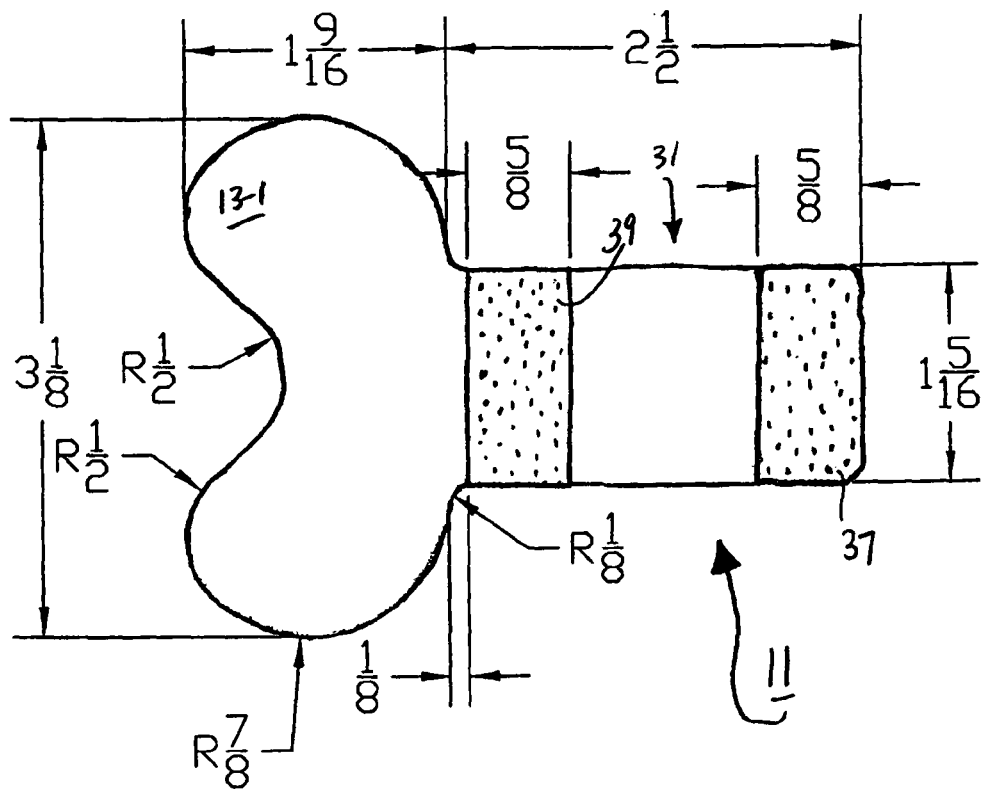
FIG. 3 is a front view of the medical appliance securing device of FIG. 1, with the medical appliance securing device being folded so that the two anchoring patches are situated back-to-back to one another and with the two anchoring patches lying substantially coplanar with the retaining tab.

Referring now to FIGS. 1 through 3, there are shown various view of a first embodiment of a medical appliance securing device constructed according to the teachings of the present invention, said medical appliance securing device being represented generally by reference numeral 11.

Device 11 comprises an anchor 13. Anchor 13, in turn, preferably comprises a pair of spaced-apart patches 13-1 and 13-2. Each of patches 13-1 and 13-2 is a multi-layered structure (seen best in FIG. 2) that preferably includes a base layer 15, an adhesive layer 17, and a moisture barrier layer 19. Base layer 15 is preferably a layer of breathable fabric and may include, for example, a layer of SONTARA® non-woven, spun-laced, hydro-entangled, polyester fabric having a basis weight of about 1.2 oz/yd² (E.I. du Pont de Nemours and Company, Wilmington, Del.). Adhesive layer 17, which is applied directly to the bottom surface of base layer 15, preferably comprises a pressure-sensitive adhesive and may be, for example, an acrylic pressure-sensitive adhesive having a thickness of about 0.001 inch. Barrier layer 19, which is positioned over the top surface of base material 15 and is adhered thereto using a tie layer 21, is a breathable material that is also water-resistant, i.e., possesses a high moisture vapor transmission rate (MVTR). For example, barrier layer 19 may be a layer of monolithic polyurethane having a thickness of about 0.001 inch. The aforementioned monolithic polyurethane may be, for example, a non-foamed, caromatiac polyether type having a Shore hardness A of 83; a specific gravity of 1.13; a 100% module-less of 1100; a 300% module-less of 2700; an ultimate tensile of 9000 (elasticity); and a tear resistance of 625.

As noted above, tie layer 21 serves to adhere barrier layer 19 to base layer 15. Accordingly, where barrier layer 19 is a layer of monolithic polyurethane of the type described above and base layer 15 includes a layer of SONTARA® non-woven, spun-laced polyester fabric, tie layer 21 may be, for example, an acrylic adhesive having a thickness of about 0.0005 inch.

Peelable release liners 25-1 and 25-2 are removably adhered to the bottoms of patches 13-1 and 13-2, respectively. When one wishes to adhere device 11 to a surface, liners 25-1 and 25-2 are peeled away, thereby exposing layer 17 of patches 13-1 and 13-2.

An example of a multi-layered material suitable for use in forming patches 13-1 and 13-2 is commercially available from DermaMed Coatings Company, LLC (Tallmadge, Ohio) as DM-6001 tape. DM-6001 tape includes a base layer of SONTARA® non-woven, spun-laced, hydro-entangled, polyester fabric having a basis weight of about 1.2 oz/yd², an acrylic pressure-sensitive adhesive layer having a thickness of about 0.001 inch applied directly to the bottom surface of the base layer, an acrylic adhesive tie layer having a thickness of about 0.0005 inch applied directly to the top surface of the base layer, and a monolithic polyurethane barrier layer having a thickness of about 0.001 inch applied directly to the top surface of the tie layer. A peelable release liner is removably adhered to the bottom surface of the pressure-sensitive adhesive layer. Using ASTM E96 (an industry standard method for assessing moisture vapor transmission rate), DM-6001 tape has an upright MVTR of 474 grams/m² over a 24-hour period and an inverted MVTR of 576 grams/m² over a 24-hour period.

Each of patches 13-1 and 13-2 is generally kidney-shaped, with patches 13-1 and 13-2 being arranged relative to one another so as to collectively assume a generally biconcave or butterfly-shape.

Device 11 also comprises a flexible retaining tab 31, tab 31 preferably extending between and interconnecting the inner edges of anchoring patches 13-1 and 13-2. Tab 31 and patches 13-1 and 13-2 preferably constitute a unitary structure, with tab 31 being formed by doubling onto itself and adhering a narrow bridge of material consisting of the same multi-layered structure used to form patches 13-1 and 13-2. Consequently, tab 31 comprises a pair of adhesive layers 17 in direct contact with one another, the adhesive layers being sandwiched between a pair of base layers 15. Base layers 15 and adhesive layers 17 are, in turn, sandwiched between a pair of tie layers 21, the entire combination of which is, in turn, sandwiched between a pair of barrier layers 19. Tab 31 has a free end 33 and a connected end 35, connected end 35 being connected to the inner edges of patches 13-1 and 13-2.

First fastening means 37 are disposed on one face of retaining tab 31 proximate to free end 33, and second fastening means 39 are disposed on the same face of retaining tab 31 proximate to connected end 35. Preferably, first fastening means 37 and second fastening means 39 comprise complementary fasteners secured to tab 31 by means of a suitable adhesive 41. Examples of complementary fasteners suitable for use as first fastening means 37 and second fastening means 39 include VELCRO® hook and loop fasteners, snap fasteners, repositionable pressure-sensitive adhesive tapes, and other fastening materials that permit repeated fastening and unfastening. Moreover, where the fastening means comprise repositionable pressure-sensitive adhesive tapes, it may be possible to eliminate second fastening means 39 and to simply adhere fastening means 37 to a desired location on retaining tab 31 or anchor 13.

Retaining tab 31 is preferably sized and fastening means 37 and 39 are preferably appropriately positioned on tab 31 so that tab 31 may be wrapped around at least a portion of the circumference of a desired medical appliance and so that fastening means 37 and 39 may then be fastened to one another in such a fashion as to secure the medical appliance to device 11.

Illustrative dimensions (in inches) for device 11 are shown in FIG. 3.

Figure 4:
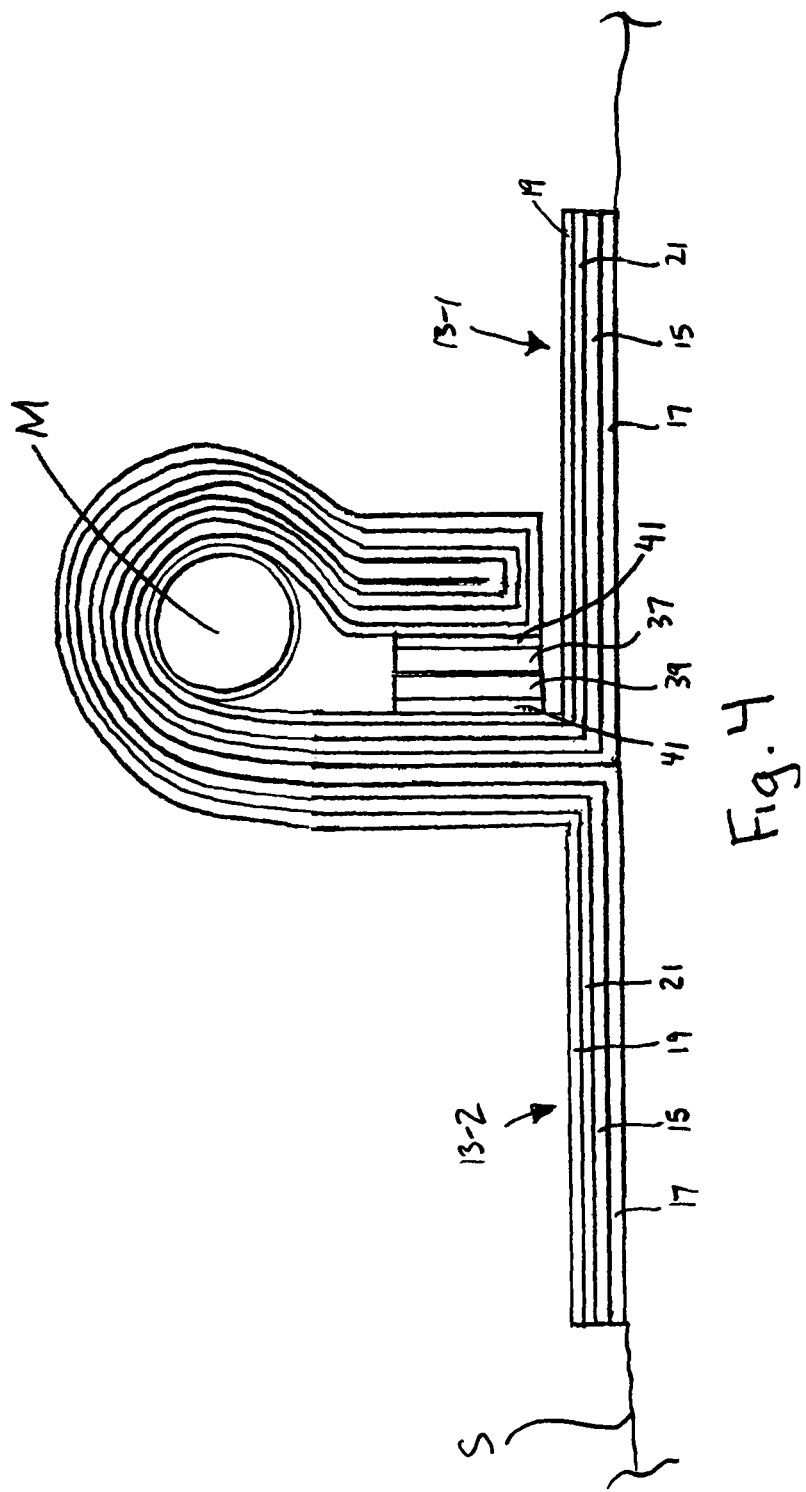
FIG. 4 is a side view, showing one way in which the medical appliance securing device of FIG. 1 may be used to secure a medical appliance to a surface.

Referring now to FIG. 4, in use, release liners 25-1 and 25-2 are peeled away from patches 13-1 and 13-2, respectively, thereby exposing adhesive layer 17 of patches 13-1 and 13-2. Next, patches 13-1 and 13-2 are preferably secured to a support surface S, such as a patient's skin or a stationary object (like a bed rail), by pressing adhesive layer 17 against the support surface S until adhesive layer 17 securely bonds thereto. Retaining tab 31 is then tightly wrapped around at least a portion of the circumference of a medical appliance M, and fasteners 37 and 39 are secured to one another.

Figure 5:
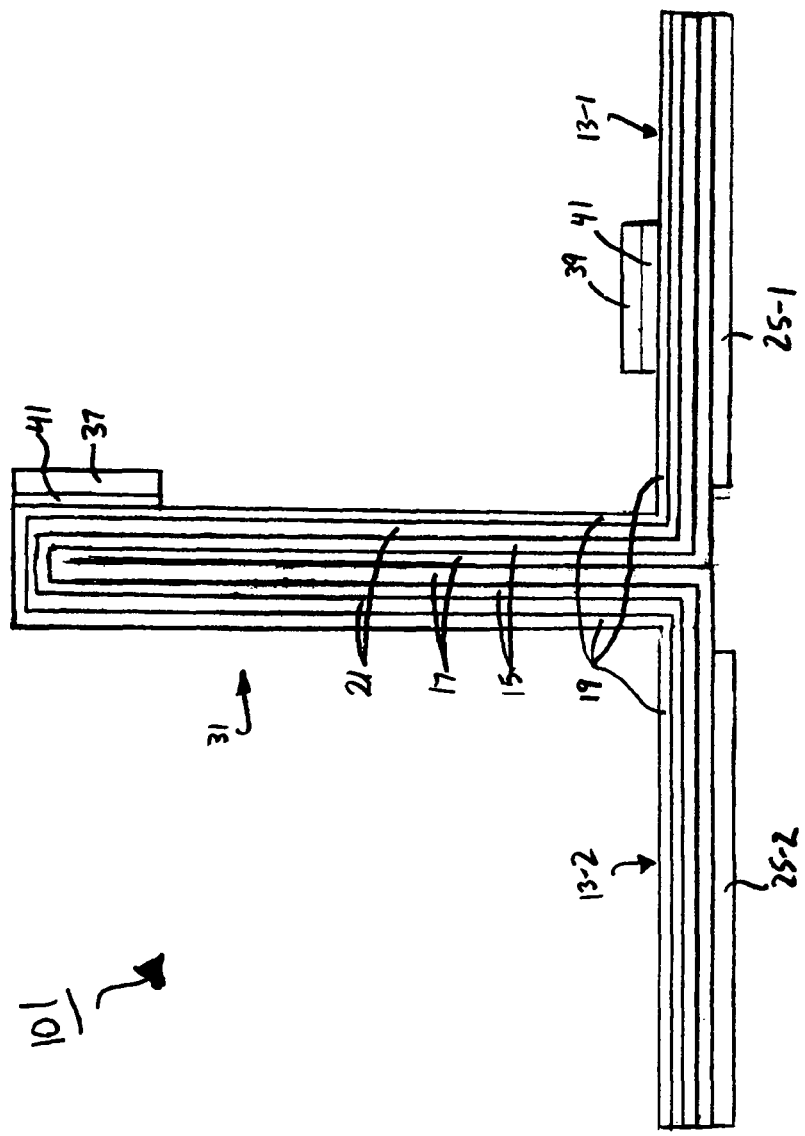
FIG. 5 is a side view of a second embodiment of a medical appliance securing device constructed according to the teachings of the present invention.

Referring now to FIG. 5, there is shown a side view of a second embodiment of a medical appliance securing device constructed according to the teachings of the present invention, said medical appliance securing device being represented generally by reference numeral 101.

Device 101 is similar in most respects to device 11, the principal difference between the two devices being that, in device 101, second fastening means 39 is secured by adhesive 41 to the top surface of patch 13-1, instead of being secured to retaining tab 31 proximate to connected end 35.

Devices 11 and 101 have a number of advantages over comparable conventional medical appliance securing devices. First, as compared to conventional devices of the type in which VELCRO® fasteners are adhered to a retaining tab and/or an anchoring patch made of DURAPORE® surgical tape, devices 11 and 101 are greatly improved at minimizing the peeling away of the VELCRO® fasteners from the retaining tab and/or an anchoring patch once the device has been exposed to water. This is largely attributable to the presence of barrier layer 19 in the present invention, barrier layer 19 minimizing the transmission of water to adhesive 41 at the interface between adhesive 41 and the retaining tab and/or anchoring patch and the resultant peeling away of the VELCRO® fasteners therefrom. To illustrate the foregoing, the following experiment was performed: A conventional CATH-SECURE™ medical appliance securing device was submerged in water for 15 seconds, patted dry and then allowed to stand for 2 to 5 min. Following such treatment of the device, the VELCRO® fasteners of the device easily peeled away from the retaining tab. By contrast, the above-described procedure was also applied to a device having the construction of device 11, said device being fabricated using DM-6001 tape. Following such treatment of device 11, the VELCRO® fasteners of device 11 did not easily peel away from the retaining tab.

A second advantage of devices 11 and 101 over conventional devices is that, whereas conventional devices have one or more anchoring patches of generally rectangular shape, devices 11 and 101 have anchoring patches that are generally kidney-shaped. This kidney shape is advantageous as it typically results in better conformance of the anchoring patches to the patient as the patient moves and, consequently, results in better adherence of the anchoring patches to the patient. By contrast, the generally rectangularly-shaped patches of conventional devices tend to peel away, particularly at their corners, from a patient over time, permitting lint and other debris to become trapped between the patches and the patient.

It is to be understood that, although the above-described embodiments of the present invention have included a single retaining tab, the present invention is not limited to embodiments having a single retaining tab, but rather, encompasses embodiments having a plurality of retaining tabs, such as in U.S. Pat. No. 5,304,146. Moreover, although the above-described embodiments of the present invention have included a retaining tab of rectangular shape, the present invention is not limited to retaining tabs having a rectangular shape, but rather, encompasses embodiments having a non-rectangular shape, such as in U.S. Pat. No. 5,304,146. Furthermore, the present invention is not limited to the placement of complementary fastening means in the positions shown in the above embodiments, but rather, encompasses at least the various locations disclosed in U.S. Pat. No. 5,304,146.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A medical appliance securing device comprising:
    (a) an anchor, said anchor being adapted to be secured to a surface, said anchor being butterfly-shaped and comprising a pair of kidney-shaped patches, each of said kidney-shaped patches having a length of 3 inches and a width of 1.5625 inch;
    (b) a single retaining tab, said single retaining tab having a first end and a second end, said first end being fixed to said anchor, said second end being free to move relative to said anchor and being appropriately spaced from said first end to permit said single retaining tab to be wrapped around at least a portion of a medical appliance; and
    (c) fastening means for securing said second end of said single retaining tab to one of said first end of said single retaining tab and said anchor;
    (d) wherein said anchor and said single retaining tab form a monolithic structure, with each of said anchor and said single retaining tab comprising an identical multi-layer structure comprising a breathable fabric, an adhesive layer, and a water-barrier layer, said adhesive layer being applied to one surface of said breathable fabric, said water-barrier layer being adhered to an opposite surface of said breathable fabric, wherein said water-barrier layer comprises a monolithic polyurethane, wherein said fastening means comprises complementary hook and loop fasteners, one of said complementary hook and loop fasteners adhered to said second end of said single retaining tab and the other of said hook and loop fasteners adhered to one of said first end of said single retaining tab and said anchor, wherein said water-barrier layer is interposed between said breathable fabric and said complementary hook and loop fastener adhered to said second end of said single retaining tab, and wherein said complementary hook and loop fastener is adhered to said water-barrier layer by an adhesive layer in direct contact with each of said water-barrier layer and said complementary hook and loop fastener.

2. The medical appliance securing device as claimed in claim 1 wherein said breathable fabric comprises a non-woven fabric.

3. The medical appliance securing device as claimed in claim 2 wherein said non-woven fabric is a spun-laced, hydro-entangled, polyester fabric.

4. The medical appliance securing device as claimed in claim 1, wherein each of said kidney-shaped patches has a top, a bottom and an inner edge, wherein said single retaining tab extends from and interconnects said inner edges of said first and second kidney-shaped patches, wherein said adhesive layer of said monolithic structure is a pressure-sensitive adhesive, and wherein said multi-layer structure is oriented in said anchor so that said pressure-sensitive adhesive is located at the bottoms of said kidney-shaped patches.

5. The medical appliance securing device as claimed in claim 4 wherein said breathable fabric comprises a non-woven fabric.

6. The medical appliance securing device as claimed in claim 5 wherein said non-woven fabric is a spun-laced, hydro-entangled, polyester fabric.

7. The medical appliance securing device as claimed in claim 1 wherein said adhesive layer comprises an acrylic pressure-sensitive adhesive.

8. The medical appliance securing device as claimed in claim 1 wherein said multi-layer structure further comprises a tie layer adhering said water-barrier layer to said breathable fabric.

9. The medical appliance securing device as claimed in claim 1 wherein one of said complementary hook and loop fasteners is adhered to said second end of said single retaining tab and the other of said hook and loop fasteners is adhered to said anchor.

10. The medical appliance securing device as claimed in claim 1 wherein one of said complementary hook and loop fasteners is adhered to said second end of said single retaining tab and the other of said hook and loop fasteners is adhered to said first end of said single retaining tab.

11. A medical appliance securing device comprising:
(a) a unitary, multi-layer structure comprising a breathable fabric, a pressure-sensitive adhesive adhered to one surface of said breathable fabric, and a water-barrier layer adhered to an opposite surface of said breathable fabric, wherein said water-barrier layer comprises a monolithic polyurethane, said unitary, multi-layer structure being shaped to include a pair of anchoring patches collectively forming an anchor of butterfly-shape and a single bridge extending from and interconnecting said anchoring patches, each of said anchoring patches being kidney-shaped and having a length of 3 inches and a width of 1.5625 inch, said single bridge being secured to itself in superposed relation to form a single retaining tab, said single retaining tab comprising a first end and a second end, said first end being fixed to said anchoring patches, said second end being free to move relative to said anchoring patches and being appropriately spaced from said first end to permit said single retaining tab to be wrapped around at least a portion of a medical appliance; and
(b) fastening means for securing said second end of said single retaining tab to one of said first end of said single retaining tab and one of said anchoring patches, wherein said fastening means comprises complementary hook and loop fasteners, one of said complementary hook and loop fasteners adhered to said second end of said single retaining tab and the other of said hook and loop fasteners adhered to one of said first end of said single retaining tab and said anchor, wherein said water-barrier layer is interposed between said breathable fabric and said complementary hook and loop fastener adhered to said second end of said single retaining tab, and wherein said complementary hook and loop fastener is adhered to said water-barrier layer by an adhesive layer in direct contact with each of said water-barrier layer and said complementary hook and loop fastener.

* * * * *